(12) United States Patent
Shovary et al.

(10) Patent No.: US 9,248,238 B2
(45) Date of Patent: Feb. 2, 2016

(54) SYRINGE WITH PASSIVE SAFETY LOCK

(75) Inventors: Cynthia Ann Shovary, Aurora, OH (US); Reggie Dwayne Huff, Vienna, OH (US)

(73) Assignee: SHOVARY & ASSOCIATES, Aurora, OH (US)

( * ) Notice: Subject to any disclaimer, the term of this patent is extended or adjusted under 35 U.S.C. 154(b) by 330 days.

(21) Appl. No.: 12/804,581

(22) Filed: Jul. 26, 2010

(65) Prior Publication Data
US 2012/0022467 A1    Jan. 26, 2012

(51) Int. Cl.
*A61M 5/315* (2006.01)

(52) U.S. Cl.
CPC ....... *A61M 5/31501* (2013.01); *A61M 5/31505* (2013.01); *A61M 2005/31506* (2013.01)

(58) Field of Classification Search
CPC ......... A61M 2005/31506; A61M 2005/31508; A61M 2005/3151; A61M 2005/2073; A61M 5/502
USPC ........................................................ 604/220
See application file for complete search history.

(56) References Cited

U.S. PATENT DOCUMENTS

| | | | |
|---|---|---|---|
| 1,798,116 A * | 3/1931 | Brockway | ...................... 604/220 |
| 2007/0049872 A1 | 3/2007 | Watts | |
| 2007/0068594 A1 | 3/2007 | Fischer | |
| 2007/0073224 A1 | 3/2007 | Dries | |
| 2007/0225656 A1 | 9/2007 | Hoyle | |
| 2007/0250002 A1* | 10/2007 | Oliver | .......................... 604/110 |
| 2007/0265580 A1 | 11/2007 | Tachikawa | |
| 2008/0021388 A1 | 1/2008 | Schwarzich | |
| 2008/0021391 A1 | 1/2008 | Polidoro | |
| 2008/0281266 A1 | 11/2008 | Walton | |
| 2009/0005759 A1 | 1/2009 | Chelak | |

* cited by examiner

*Primary Examiner* — Nathan R Price

(57) ABSTRACT

A new syringe design is provided with a safety feature that prevents inadvertent or otherwise unintended release of any contents within the syringe. This safety feature is accomplished by way of an automatic (passive) plunger locking mechanism. The new syringe design also providing for automatic (passive) disengagement of the automatic plunger locking mechanism so as to not inhibit the operating use and function of a syringe.

3 Claims, 3 Drawing Sheets

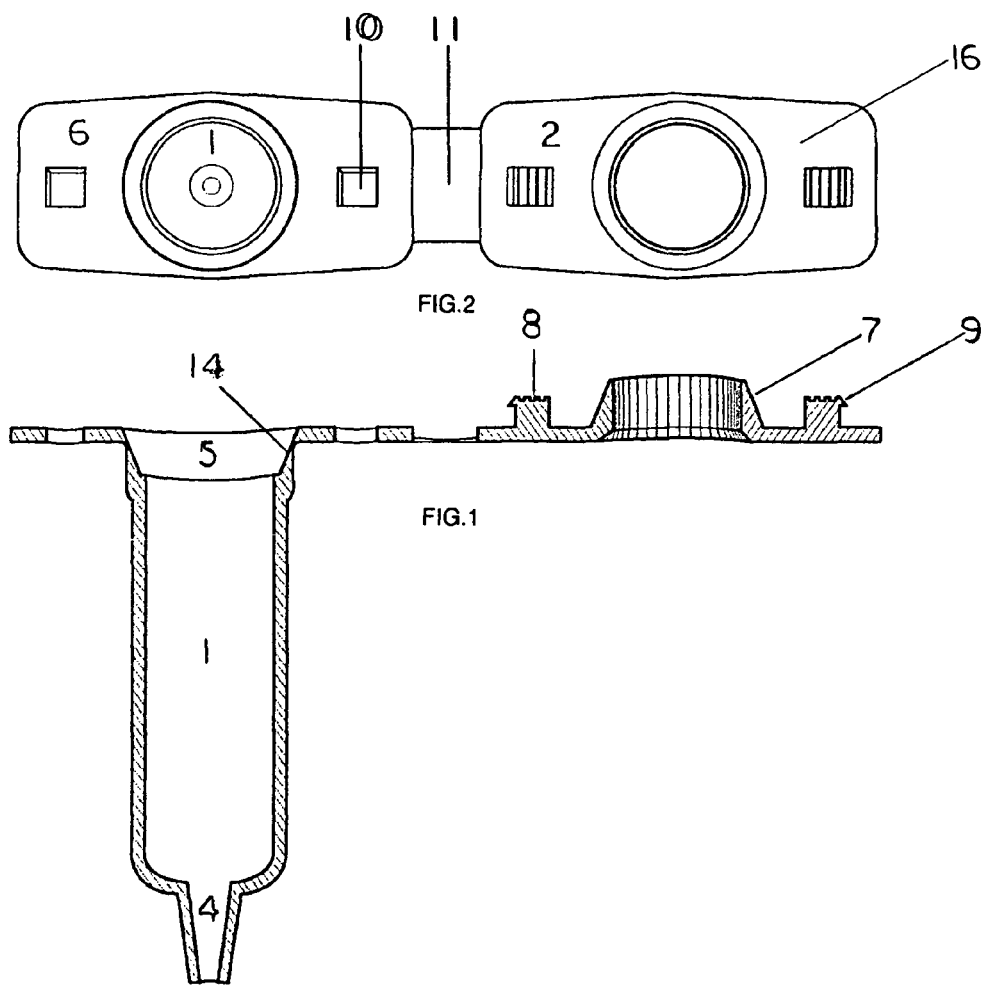

SYRINGE WITH PASSIVE SAFETY LOCK

BACKGROUND

The invention here disclosed relates primarily to syringes and in particular those typically used for medical purposes that allow unintended dispensement of fluid substances from the syringes main staging chamber.

The main purpose of the improvement here disclosed is to provide a reliable, safe, simple and low cost method of passively and automatically locking a syringe from unintended dispensement of its contents when and only when not engaged for its ultimate purpose and allowing for automatic unlocking whenever and however many times a syringe is engaged for its ultimate purpose upon at least two points of contact.

Various attempts to create syringe locks have been made such as the locking mechanism disclosed by Watts (20070049872-A1 US). These attempts allow effective locking control by way of the deliberative action of the user to engage the locking mechanism. Further, the locking mechanism is disclosed as a separate part which will lead to inconsistent use where safety is a factor.

The invention here disclosed provides passive locking and unlocking control of the syringe plunger in its preferred embodiments. Further, the preferred embodiments accomplish the said passive locking control within a simple low cost and easy to manufacture and implement structure.

Passive locking control is necessary to ensure maximum effective use, application safety enhancement and reduced waste including that of sometimes expensive medical supplies.

BRIEF DESCRIPTION OF DRAWINGS

FIG. 1 is a sectional side view of a preferred embodiment of a syringe cylinder, casing and the attached locking slip collar in its post injection mold manufacture position.

FIG. 2 is a top view of the syringe cylinder and casing depicted in FIG. 1.

FIG. 4 also provides directional arrows depicting the finger pressure as applied when the syringe is engaged for its intended purpose.

DETAILED DESCRIPTION OF PREFERRED EMBODIMENTS

As illustrated by FIGS. 1,2, 3 & 4 a syringe, cylinder, 1 is molded with a locking slip collar 2, attached in a manner to allow purposeful concentric engagement with the open end of the syringe cylinder 5 after the plastic molding process is complete as illustrated in 3.

Figure 3:
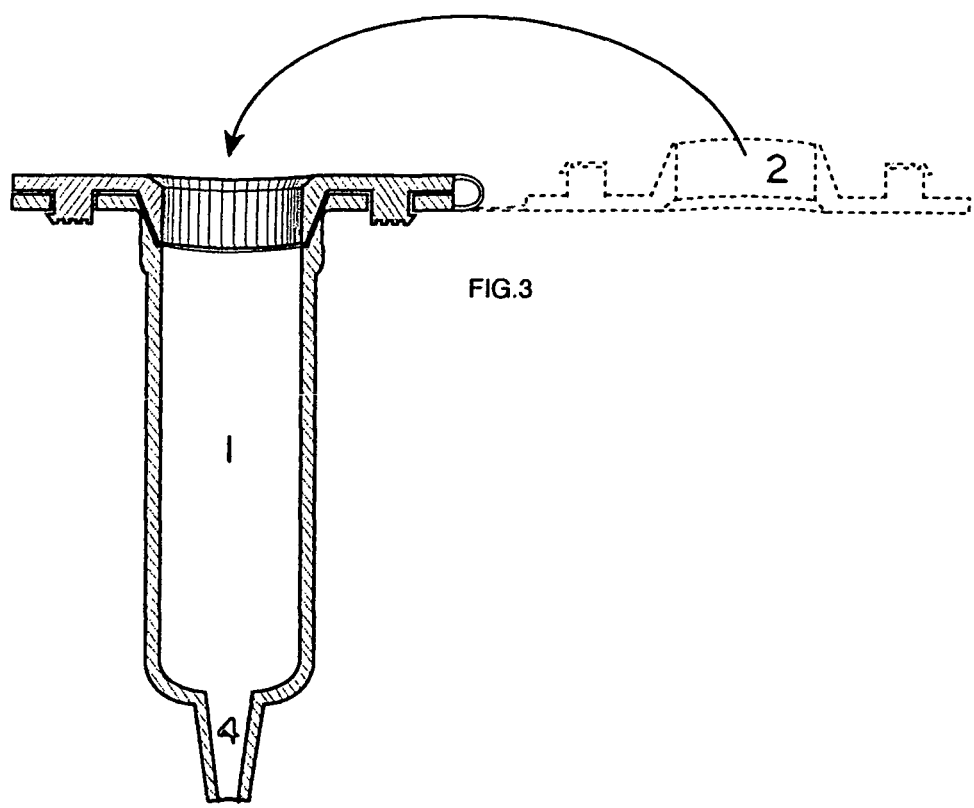
FIG. 3 is a cross sectional side view of the syringe cylinder and casing depicted in FIG. 1 with the locking slip collar depicted in locked working engagement with the open cylinder end and its corresponding wedge seat.

As illustrated in FIGS. 1,2 & 3 once the locking slip collar 2, is rotated and locked into its final working position the attaching flexible plastic strip 11, acts both as a hinge and spring in order to bias the locking slip collar in the preferred opposite direction away from the syringe cylinder-case's open end 5.

Figures 4, 4A:
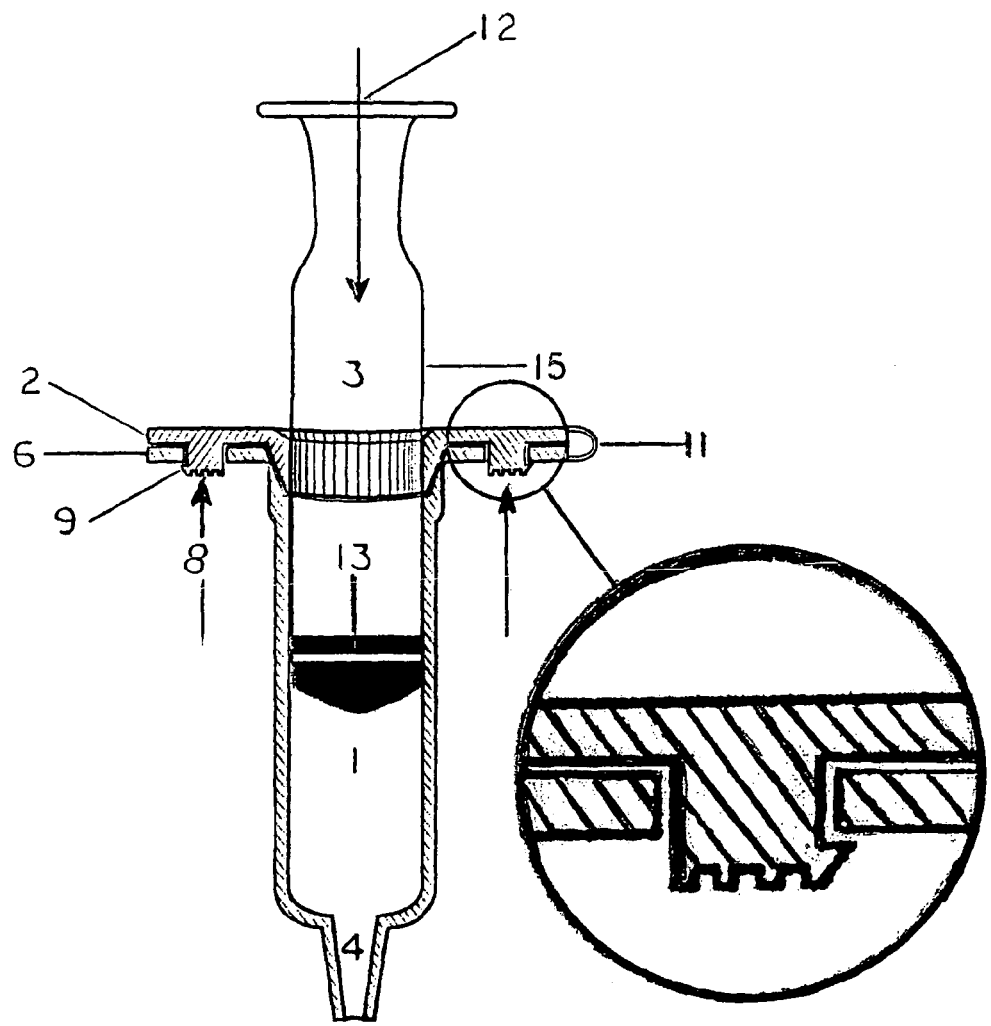
FIGS. 4 & 4A is a side view of the syringe cylinder and casing depicted in FIG. 3 with the plunger assembly installed that provides an expanded view of the locked working engagement of the locking slip collar.

As illustrated in FIGS. 1 & 4 a plunger arrangement 3, is inserted into and past the locking slip collar 2, and into the cylinder simultaneously. The locking slip collar 2, is designed with a slight interference fit around the plunger's concentrically round tube base 15. Anytime the plunger arrangement 3 is unintentionally displaced linearly toward the distal end of the cylinder 4, the locking slip collar 2, is automatically driven into a wedge seat arrangement designed within the open end of the cylinder 14, designed to engage a corresponding wedge seat as part of the locking slip collar 7. The engagement of the cylinder open end wedge seat applies pressure to the full circumference of the outer periphery of the locking slip collar which exponentially increases resistance between the locking slip collar 2, and the plunger's concentrically round tube base 15, as pressure is applied to the plunger 3, which ultimately locks the said plunger arrangement and disallows further unintentional displacement of the plunger arrangement therein 3, towards the distal end of the cylinder 4, which prevents unintentional dispensement of the contents therein.

As illustrated in FIGS. 1, 2, 3 & 4 once the locking slip collar 2 is rotated into its final working position the locking slip collar includes unidirectional locks 9, as part of locking slip collar finger pads 8 & 4A, which pass through reliefs 10, provided within the cylinder flanges 6, which disallows separation of the locking slip collar 2, from the cylinder flanges but allows at least the minimum linear movement of the locking slip collar relative to the cylinder 1, in order to allow repeated positive seating of the locking slip caller to activate the locking function and unseating of the same slip collar to deactivate the locking function, FIG. 4A.

After full assembly of the syringe as illustrated in FIG. 4, manual manipulation or engagement of the syringe for its intended purpose results in finger pressure being applied to the protruding finger pads 8 & 4A, and the exposed end of the plunger 12, which automatically and reliably displaces the locking slip collar 2, in the opposite direction of the wedge seat engagement 14, and in the opposite direction of the plunger's 3 linear intended movement toward the distal end of the cylinder 4. which facilitates disengagement and/or deactivation of the locking slip collar allowing low resistance linear displacement of the plunger 3, towards the distal end of the syringe cylinder 4, to a selectively desired displacement.

As illustrated in FIG. 4 in the preferred embodiment the plunger 3, includes a simple one way locking lip, 13, at it's distil end which allows the plunger, #3, to pass through the locking slip collar 2, during initial assembly and allows a full range of dual direction slidable connection with the locking slip collar 2, but disallows reverse direction disengagement of the plunger passed the locking lip 13, in order to discourage disassembly of the primary purpose passive safety feature as may be desired.

What is claimed is:

1. A syringe assembly comprising:
   a syringe cylinder including an open end with at least one flange and a reduced orifice distal end opposite the open end, the syringe cylinder configured to allow fluid communication to and through the reduced orifice distal end,
   a syringe plunger within the syringe cylinder for sealed slidable linear longitudinal displacement through the open end of the syringe cylinder and towards the reduced orifice distal end of the syringe cylinder, the syringe plunger comprising an exposed end for manual manipulation,
   the at least one flange of the open end of the syringe cylinder and the exposed end of the syringe plunger together allowing manual engagement of the syringe assembly for manual manipulation of the sealed slidable linear longitudinal displacement of the syringe plunger within the syringe cylinder towards the reduced orifice distal end of the syringe cylinder, and a locking slip collar around the syringe plunger forming an interference fit with the syringe plunger that allows low resistance longitudinal movement of the syringe plunger therethrough, the locking slip collar comprising a wedge seat configured upon an outer periphery of the locking slip collar;

wherein the open end of the syringe cylinder further comprises a corresponding wedge seat corresponding to the wedge seat of the locking slip collar, the wedge seat of the locking slip collar being biased away from the corresponding wedge seat of the open end of the syringe cylinder towards the exposed end of the plunger, wherein movement of the locking slip collar towards the reduced orifice distal end resulting from pressure applied to the exposed end of the syringe plunger and through the interference fit between the locking slip collar and the syringe plunger mates the corresponding wedge seat of the open end of the syringe cylinder with the wedge seat of the locking slip collar to apply pressure to the wedge seat of the locking slip collar that increases resistance of the interference fit between the locking slip collar and the syringe plunger, thereby locking the syringe plunger against unintentional displacement towards the reduced orifice distal end of the syringe cylinder, and wherein the locking slip collar further comprises at least one protruding finger pad disposed through at least one relief in the at least one flange of the open end of the syringe cylinder to lock the locking slip collar against disengagement from the syringe cylinder, wherein manual manipulation or engagement of the syringe assembly to apply pressure in a first direction against the exposed end of the plunger toward the reduced orifice distal end of the syringe cylinder in combination with pressure against the at least one finger pad of the locking slip collar in a second direction opposite the first direction displaces the wedge seat of the locking slip collar in the second direction away from the corresponding wedge seat of the open end of the syringe cylinder, reducing resistance of the interference fit between the locking slip collar and the syringe plunger to allow displacement of the syringe plunger in the first direction towards the reduced orifice distal end of the syringe cylinder.

2. The syringe assembly in claim 1, wherein the at least one flange comprises a first flange, and the syringe assembly further comprises a flexible plastic strip connecting the locking slip collar to the first flange, the flexible plastic strip acting both as a hinge and a spring to allow the locking slip collar to be rotated into engagement with the open end of the syringe cylinder during assembly and to bias the locking slip collar away from the open end of the syringe cylinder.

3. The syringe assembly in claim 1, wherein the at least one finger pad of the locking slip collar comprises a first finger pad and the at least one relief comprises a first relief, the first finger pad including a unidirectional lock which passes through the first relief and disallows separation of the locking slip collar from the at least one flange of the open end of the syringe cylinder but allows linear movement of the locking slip collar relative to the cylinder in order to allow repeated activation and deactivation of mating of the wedge seat of the locking slip collar with the corresponding wedge seat of the open end of the syringe cylinder.

* * * * *